(12) United States Patent
Grover et al.

(10) Patent No.: US 9,005,215 B2
(45) Date of Patent: Apr. 14, 2015

(54) SPECIMEN RETRIEVAL APPARATUS

(75) Inventors: Simon Roderick Grover, Cambridge (GB); Oliver Brian Godbold, Cambridge (GB); Alistair Ian Fleming, Cambridge (GB); Charles Alan Seegert, Irving, TX (US)

(73) Assignee: Covidien LP, Mansfield, MA (US)

( * ) Notice: Subject to any disclaimer, the term of this patent is extended or adjusted under 35 U.S.C. 154(b) by 323 days.

(21) Appl. No.: 13/235,590

(22) Filed: Sep. 19, 2011

(65) Prior Publication Data

US 2012/0083796 A1    Apr. 5, 2012

Related U.S. Application Data

(60) Provisional application No. 61/389,391, filed on Oct. 4, 2010.

(51) Int. Cl.
*A61B 17/50* (2006.01)
*A61B 17/00* (2006.01)
*A61B 17/29* (2006.01)

(52) U.S. Cl.
CPC . *A61B 17/00234* (2013.01); *A61B 2017/00287* (2013.01); *A61B 2017/00292* (2013.01); *A61B 2017/2923* (2013.01); *A61B 2017/2927* (2013.01)

(58) Field of Classification Search
CPC .................. A61B 17/00234; A61B 2017/2927; A61B 2017/2923; A61B 2017/2925; A61B 2017/2912; A61B 2017/00292; A61B 2017/00287
USPC ......... 606/110, 114, 127, 128, 141, 142, 200, 606/108; 604/317, 540; 600/562
See application file for complete search history.

(56) References Cited

U.S. PATENT DOCUMENTS

| | | | |
|---|---|---|---|
| 30,471 A | 10/1860 | Dudley | |
| 156,477 A | 11/1874 | Bradford | |
| 1,609,014 A | 11/1926 | Dowd | |
| 3,800,781 A | 4/1974 | Zalucki | |
| 35,164 A | 5/1982 | Logan et al. | |
| 4,557,255 A | 12/1985 | Goodman | |

(Continued)

FOREIGN PATENT DOCUMENTS

| DE | 8435489 | 12/1984 |
|---|---|---|
| DE | 3542667 | 6/1986 |

(Continued)

OTHER PUBLICATIONS

Extended European Search Report corresponding to EP No. 11 25 0837.9, completed Sep. 3, 2013 and mailed Sep. 10, 2013; (7 pp).

(Continued)

*Primary Examiner* — Ryan Severson
*Assistant Examiner* — Anh Dang (57) ABSTRACT

A specimen retrieval apparatus includes a housing having an elongated tubular member extending distally therefrom. The elongated tubular member defines a longitudinal axis. An end effector assembly is coupled to a distal end of the elongated tubular member. The end effector assembly is configured to retain a specimen retrieval bag thereon. An articulation mechanism is operatively coupled to the elongated tubular member and the end effector assembly. The articulation mechanism is configured for selectively articulating the end effector assembly with respect to the longitudinal axis of the elongated tubular member.

8 Claims, 11 Drawing Sheets

(56) References Cited

U.S. PATENT DOCUMENTS

| | | |
|---|---|---|
| 4,611,594 A | 9/1986 | Grayhack et al. |
| 4,744,363 A | 5/1988 | Hasson |
| 4,790,812 A | 12/1988 | Hawkins, Jr. et al. |
| 4,927,427 A | 5/1990 | Kriauciunas et al. |
| 4,997,435 A | 3/1991 | Demeter |
| 5,037,379 A | 8/1991 | Clayman et al. |
| 5,074,867 A | 12/1991 | Wilk |
| 5,084,054 A | 1/1992 | Bencini et al. |
| 5,143,082 A | 9/1992 | Kindberg et al. |
| 5,147,371 A | 9/1992 | Washington et al. |
| 5,176,687 A | 1/1993 | Hasson et al. |
| 5,190,542 A | 3/1993 | Nakao et al. |
| 5,190,555 A | 3/1993 | Wetter et al. |
| 5,190,561 A | 3/1993 | Graber |
| 5,192,284 A | 3/1993 | Pleatman |
| 5,192,286 A | 3/1993 | Phan et al. |
| 5,201,740 A | 4/1993 | Nakao et al. |
| 5,215,521 A | 6/1993 | Cochran et al. |
| 5,234,439 A | 8/1993 | Wilk et al. |
| 5,279,539 A | 1/1994 | Bohan et al. |
| 5,312,416 A | 5/1994 | Spaeth et al. |
| 5,330,483 A | 7/1994 | Heaven et al. |
| 5,336,227 A | 8/1994 | Nakao et al. |
| 5,337,754 A | 8/1994 | Heaven et al. |
| 5,341,815 A | 8/1994 | Cofone et al. |
| 5,352,184 A | 10/1994 | Goldberg et al. |
| 5,354,303 A | 10/1994 | Spaeth et al. |
| 5,368,545 A | 11/1994 | Schaller et al. |
| 5,368,597 A | 11/1994 | Pagedas |
| 5,370,647 A | 12/1994 | Graber et al. |
| 5,465,731 A | 11/1995 | Bell et al. |
| 5,480,404 A | 1/1996 | Kammerer et al. |
| 5,486,182 A | 1/1996 | Nakao et al. |
| 5,486,183 A | 1/1996 | Middleman et al. |
| 5,499,988 A | 3/1996 | Espiner et al. |
| 5,524,633 A | 6/1996 | Heaven et al. |
| 5,535,759 A | 7/1996 | Wilk |
| 5,611,803 A | 3/1997 | Heaven et al. |
| 5,618,296 A | 4/1997 | Sorensen et al. |
| 5,630,822 A | 5/1997 | Hermann et al. |
| 5,643,282 A | 7/1997 | Kieturakis |
| 5,643,283 A | 7/1997 | Younker |
| 5,645,083 A | 7/1997 | Essig et al. |
| 5,647,372 A | 7/1997 | Tovey et al. |
| 5,649,902 A | 7/1997 | Yoon |
| 5,658,296 A | 8/1997 | Bates et al. |
| 5,679,423 A | 10/1997 | Shah |
| 5,735,289 A | 4/1998 | Pfeffer et al. |
| 5,755,724 A | 5/1998 | Yoon |
| 5,759,187 A | 6/1998 | Nakao et al. |
| 5,769,794 A | 6/1998 | Conlan et al. |
| 5,785,677 A | 7/1998 | Auweiler |
| 5,788,709 A | 8/1998 | Riek et al. |
| 5,792,145 A | 8/1998 | Bates et al. |
| 5,814,044 A | 9/1998 | Hooven |
| 5,836,953 A | 11/1998 | Yoon |
| 5,853,374 A | 12/1998 | Hart et al. |
| 5,895,392 A | 4/1999 | Riek et al. |
| 5,906,621 A | 5/1999 | Secrest et al. |
| 5,957,884 A | 9/1999 | Hooven |
| 5,971,995 A | 10/1999 | Rousseau |
| 5,980,544 A | 11/1999 | Vaitekunas |
| 5,997,547 A | 12/1999 | Nakao et al. |
| 6,004,330 A | 12/1999 | Middleman et al. |
| 6,007,512 A | 12/1999 | Hooven |
| 6,019,770 A | 2/2000 | Christoudias |
| 6,036,681 A | 3/2000 | Hooven |
| 6,059,793 A | 5/2000 | Pagedas |
| 6,123,701 A | 9/2000 | Nezhat |
| 6,152,932 A | 11/2000 | Ternström |
| 6,162,235 A | 12/2000 | Vaitekunas |
| 6,165,121 A | 12/2000 | Alferness |
| 6,168,603 B1 | 1/2001 | Leslie et al. |
| 6,228,095 B1 | 5/2001 | Dennis |
| 6,270,505 B1 | 8/2001 | Yoshida et al. |
| 6,277,083 B1 | 8/2001 | Eggers et al. |
| 6,280,450 B1 | 8/2001 | McGuckin, Jr. |
| 6,344,026 B1 | 2/2002 | Burbank et al. |
| 6,348,056 B1 | 2/2002 | Bates et al. |
| 6,350,266 B1 | 2/2002 | White et al. |
| 6,350,267 B1 | 2/2002 | Stefanchik |
| 6,383,195 B1 | 5/2002 | Richard |
| 6,383,196 B1 | 5/2002 | Leslie et al. |
| 6,383,197 B1 | 5/2002 | Conlon et al. |
| 6,406,440 B1 | 6/2002 | Stefanchik |
| 6,409,733 B1 | 6/2002 | Conlon et al. |
| 6,419,639 B2 | 7/2002 | Walther et al. |
| 6,447,523 B1 | 9/2002 | Middleman et al. |
| 6,471,659 B2 | 10/2002 | Eggers et al. |
| 6,506,166 B1 | 1/2003 | Hendler et al. |
| 6,508,773 B2 | 1/2003 | Burbank et al. |
| 6,537,273 B1 | 3/2003 | Sosiak et al. |
| 6,589,252 B2 | 7/2003 | McGuckin, Jr. |
| 6,752,811 B2 | 6/2004 | Chu et al. |
| 6,755,779 B2 | 6/2004 | Vanden Hoek et al. |
| 6,780,193 B2 | 8/2004 | Leslie et al. |
| 6,805,699 B2 | 10/2004 | Shimm |
| 6,840,948 B2 | 1/2005 | Albrecht et al. |
| 6,872,211 B2 | 3/2005 | White et al. |
| 6,887,255 B2 | 5/2005 | Shimm |
| 6,994,696 B2 | 2/2006 | Suga |
| 7,052,454 B2 | 5/2006 | Taylor |
| 7,052,501 B2 | 5/2006 | McGuckin, Jr. |
| 7,090,637 B2 | 8/2006 | Danitz et al. |
| 7,270,663 B2 | 9/2007 | Nakao |
| 7,273,488 B2 | 9/2007 | Nakamura et al. |
| 7,410,491 B2 | 8/2008 | Hopkins et al. |
| 7,547,310 B2 | 6/2009 | Whitfield |
| 2003/0109888 A1* | 6/2003 | Mercereau et al. ........... 606/127 |
| 2004/0097960 A1 | 5/2004 | Terachi et al. |
| 2004/0138587 A1 | 7/2004 | Lyons |
| 2005/0267492 A1 | 12/2005 | Poncet et al. |
| 2006/0052799 A1 | 3/2006 | Middleman et al. |
| 2006/0058776 A1 | 3/2006 | Bilsbury |
| 2006/0200169 A1 | 9/2006 | Sniffin |
| 2006/0200170 A1 | 9/2006 | Aranyi |
| 2006/0229639 A1 | 10/2006 | Whitfield |
| 2006/0229640 A1 | 10/2006 | Whitfield |
| 2007/0016224 A1 | 1/2007 | Nakao |
| 2007/0016225 A1 | 1/2007 | Nakao |
| 2007/0073251 A1 | 3/2007 | Zhou et al. |
| 2007/0088370 A1 | 4/2007 | Kahle et al. |
| 2007/0135780 A1 | 6/2007 | Pagedas |
| 2007/0135781 A1 | 6/2007 | Hart |
| 2008/0188766 A1 | 8/2008 | Gertner |
| 2008/0221588 A1 | 9/2008 | Hollis et al. |
| 2008/0234696 A1 | 9/2008 | Taylor et al. |
| 2008/0300621 A1 | 12/2008 | Hopkins et al. |
| 2008/0312496 A1 | 12/2008 | Zwolinski |
| 2009/0082779 A1 | 3/2009 | Nakao |
| 2009/0182292 A1 | 7/2009 | Egle et al. |
| 2009/0192510 A1 | 7/2009 | Bahney |
| 2009/0240238 A1 | 9/2009 | Grodrian et al. |
| 2010/0000471 A1 | 1/2010 | Hibbard |
| 2010/0152746 A1* | 6/2010 | Ceniccola et al. ............ 606/114 |

FOREIGN PATENT DOCUMENTS

| | | |
|---|---|---|
| EP | 2184014 | 5/2010 |
| FR | 1272412 | 9/1961 |
| WO | WO 93/15675 | 8/1993 |
| WO | WO 95/09666 | 4/1995 |
| WO | WO 2004/002334 A1 | 1/2004 |
| WO | WO 2004/112571 | 12/2004 |
| WO | WO 2005/112783 A1 | 12/2005 |
| WO | WO 2008/114234 | 9/2008 |

OTHER PUBLICATIONS

Extended European Search Report corresponding to EP No. 11 25 0838.7, completed Sep. 3, 2013 and mailed Sep. 10, 2013; (5 pp).

* cited by examiner

SPECIMEN RETRIEVAL APPARATUS

This application claims priority from provisional application Ser. No. 61/389,391, filed Oct. 4, 2010, the entire contents of which are incorporated herein by reference.

BACKGROUND

1. Technical Field

The present disclosure relates to a retrieval apparatus, and more particularly, to a specimen retrieval apparatus for use in minimally invasive surgical procedures.

2. Background of Related Art

In minimally invasive surgical procedures, operations are carried out within the body by using elongated instruments inserted through small entrance openings in the body. The initial opening in the body tissue to allow passage of instruments to the interior of the body may be a natural passageway of the body, or it can be created by a tissue piercing instrument such as a trocar, or created by a small incision into which a cannula is inserted.

Because the tubes, instrumentation, and any required punctures or incisions are relatively small, the surgery is less invasive as compared to conventional surgical procedures in which the surgeon is required to cut open large areas of body tissue. Therefore, minimally invasive surgery minimizes trauma to the patient and reduces patient recovery time and hospital costs.

Minimally invasive procedures may be used for partial or total removal of body tissue or organs from the interior of the body, e.g. nephrectomy, cholecystectomy, lobectomy and other procedures including thoracic, laparoscopic and endoscopic procedures. During such procedures, it is common that a cyst, tumor, or other affected tissue or organ needs to be removed via the access opening in the skin, or through a cannula. Various types of entrapment devices have been disclosed to facilitate this procedure. In many procedures where cancerous tumors are removed, removal of the specimen in an enclosed environment is highly desirable to prevent seeding of cancer cells.

In minimally invasive thoracic surgery, access to the thoracic cavity is limited as well as maneuverability within the cavity as the access port is placed between the confined space between a patient's ribs. Such procedures, commonly referred to as video assisted thoracoscopic surgery (VATS), aim to reduce patient recovery time by accessing the thoracic cavity through the natural intercostal space without spreading the ribs as in open procedures. This restricted access can sometimes cause problems when removing large specimens. Moreover, in such procedures, e.g. thoracoscopic wedge resection and lobectomy, it is often necessary to remove a portion of the lung and retrieve it relatively intact for pathology. It is also desirable that the specimen be sufficiently contained to prevent seeding of cancer cells during manipulation and removal.

In designing such specimen retrieval instrumentation, a balance must be struck between the need to provide a retrieval apparatus with a strong enough containment bag to prevent tearing or rupture while providing sufficient rigidity to enable manipulation and removal. Another balance which needs to be achieved is to provide sufficient maneuverability while reducing tissue trauma, e.g. damaging lung tissue, during manipulation and removal. Additionally, the instrumentation on one hand should be able to be inserted through a small access incision or port while on the other hand able to accommodate a wide range of patient sizes and be able to easily remove large specimens and minimize risk of seeding.

SUMMARY

In accordance with one aspect of the present disclosure, a specimen retrieval apparatus is provided. The specimen retrieval apparatus includes a housing having an elongated tubular member extending distally therefrom. The elongated tubular member defines a longitudinal axis and has an end effector assembly coupled to a distal end thereof. The end effector assembly is configured to retain a specimen retrieval bag thereon. An articulation mechanism is operatively coupled to the end effector assembly and is configured for selectively incrementally articulating the end effector assembly with respect to the longitudinal axis of the elongated tubular member.

In one embodiment, the articulation mechanism includes a gear assembly. The gear assembly can include a gear rack engaged to the end effector assembly and a worm gear in meshed engagement with the gear rack such that rotation of the worm gear about the longitudinal axis effects longitudinal translation of the gear rack.

The articulation mechanism can include a rotatable actuator operatively disposed on the housing and coupled to the articulation mechanism. The rotatable actuator is preferably selectively rotatable, e.g., by a hand of the user, for articulating the end effector with respect to the longitudinal axis of the elongated tubular member.

The specimen retrieval apparatus can include a drive assembly operatively engaged to the elongated tubular member and configured to move the end effector assembly from a retracted position to an extended position.

In some embodiments, the end effector assembly includes a pair of arms configured to retain the specimen retrieval bag thereon and moveable between an approximated position, corresponding to the retracted position of the end effector assembly, and a spaced-apart position, corresponding to the extended position of the end effector assembly. In some embodiments, a trigger may be provided for selectively moving the end effector from the retracted position to the extended position.

In some embodiments, the drive assembly can include a ratchet mechanism for incrementally translating the end effector assembly between the retracted position and the extended position. Accordingly, in embodiments where the trigger is provided, the trigger can be selectively depressed through a plurality of positions, each position corresponding to an incremental position of the end effector assembly between the retracted position and the extended position.

In some embodiments, the elongated tubular member defines a lumen extending therethrough configured to permit passage of surgical instrumentation, e.g., a vacuum tube or other surgical instrument, therethrough.

In some embodiments, an elongated sleeve extends distally from the housing. The elongated sleeve is disposed about at least a portion of the elongated tubular member.

In accordance with another aspect of the present disclosure, a surgical retrieval apparatus is provided including a housing having an elongated tubular member extending therefrom and an end effector assembly disposed at a distal end of the elongated tubular member. A drive assembly is configured for moving the end effector assembly from a retracted position to an extended position. A specimen retrieval bag is positioned at the end effector assembly. The specimen retrieval bag is deployable from an undeployed position to a deployed position. The specimen retrieval bag includes a channel disposed therein to facilitate escape of air from a portion of the retrieval bag through the channel, the channel having a proximal opening and at least one opening distal of the proximal opening.

The retrieval apparatus can include an articulation mechanism configured for selectively incrementally articulating the end effector assembly with respect to the longitudinal axis.

In some embodiments, the articulation mechanism includes a rotatable actuator translatable to return the end effector assembly to the retracted position.

In some embodiments, an elongated shape of material is positioned within the channel to support the channel. In some embodiments, the material is an open cell material such as an open cell foam to enable passage of air therethrough. In some embodiments, a transverse dimension of the elongated shape of material is less than a transverse dimension of the channel.

The channel can be formed integral from a material of the bag. Alternatively, the channel can be formed from a tube or material attached to an interior surface of the bag.

In some embodiments, the specimen retrieval bag has a proximal region and a distal region, wherein the distal region is narrower in transverse dimension than the proximal region and the channel is elongated and extends from the proximal region to the distal region. In some embodiments, the channel can be positioned at an acute angle to the longitudinal axis of the bag.

BRIEF DESCRIPTION OF THE DRAWINGS

Various embodiments of the subject specimen retrieval apparatus are described herein with reference to the drawings wherein.

DETAILED DESCRIPTION

Various embodiments of the presently disclosed specimen retrieval apparatus, and methods of using the same, will now be described in detail with reference to the drawings wherein like references numerals identify similar or identical elements. In the drawings, and in the following description, the term "proximal" should be understood as referring to the end of the apparatus, or component thereof, that is closer to the clinician during proper use, while the term "distal" should be understood as referring to the end that is farther from the clinician, as is traditional and conventional in the art.

Figure 1A:
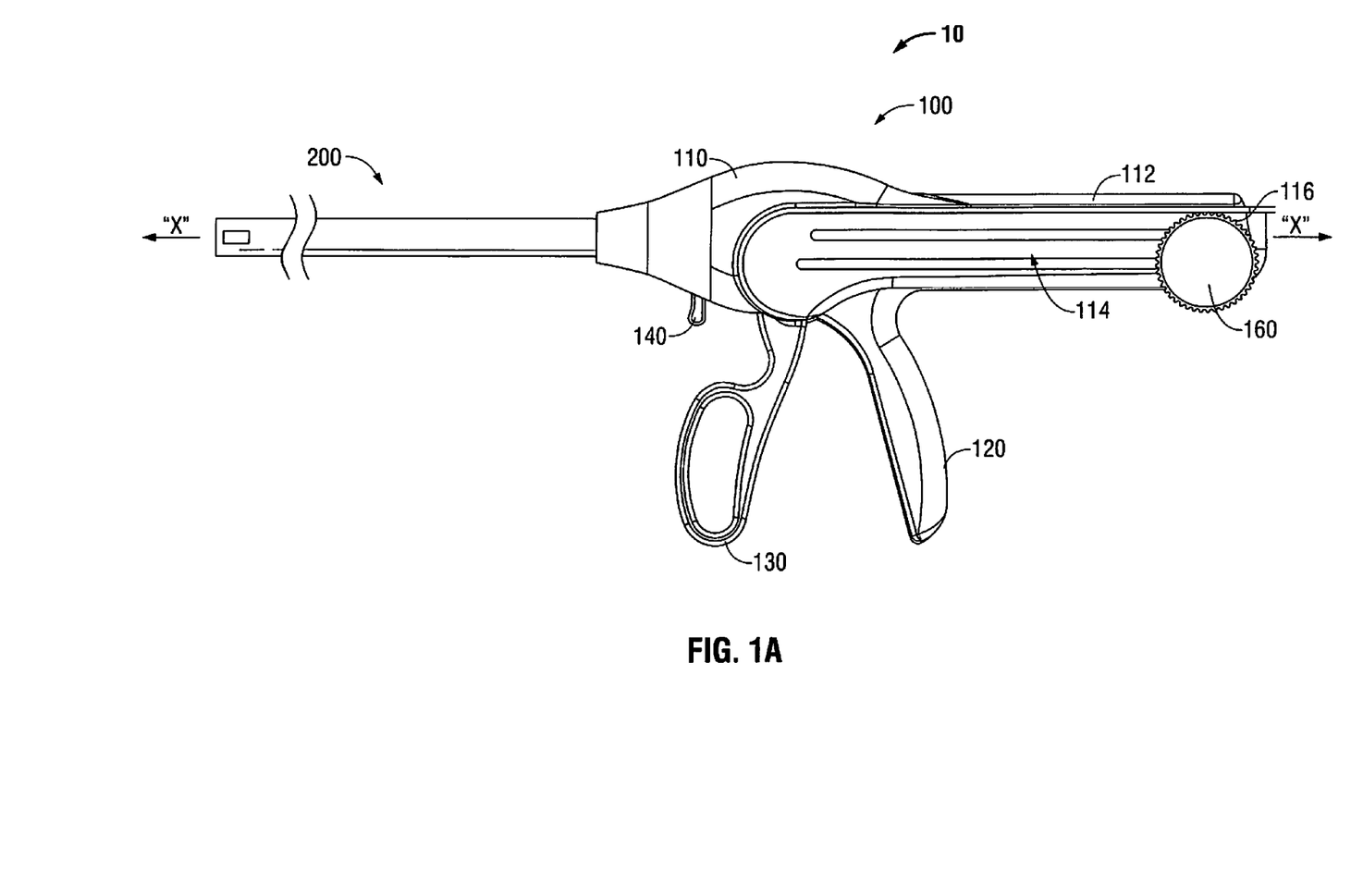
FIG. 1A is a perspective view of a specimen retrieval apparatus in accordance with the present disclosure with the end effector contained within the outer sleeve.
Figure 1B:
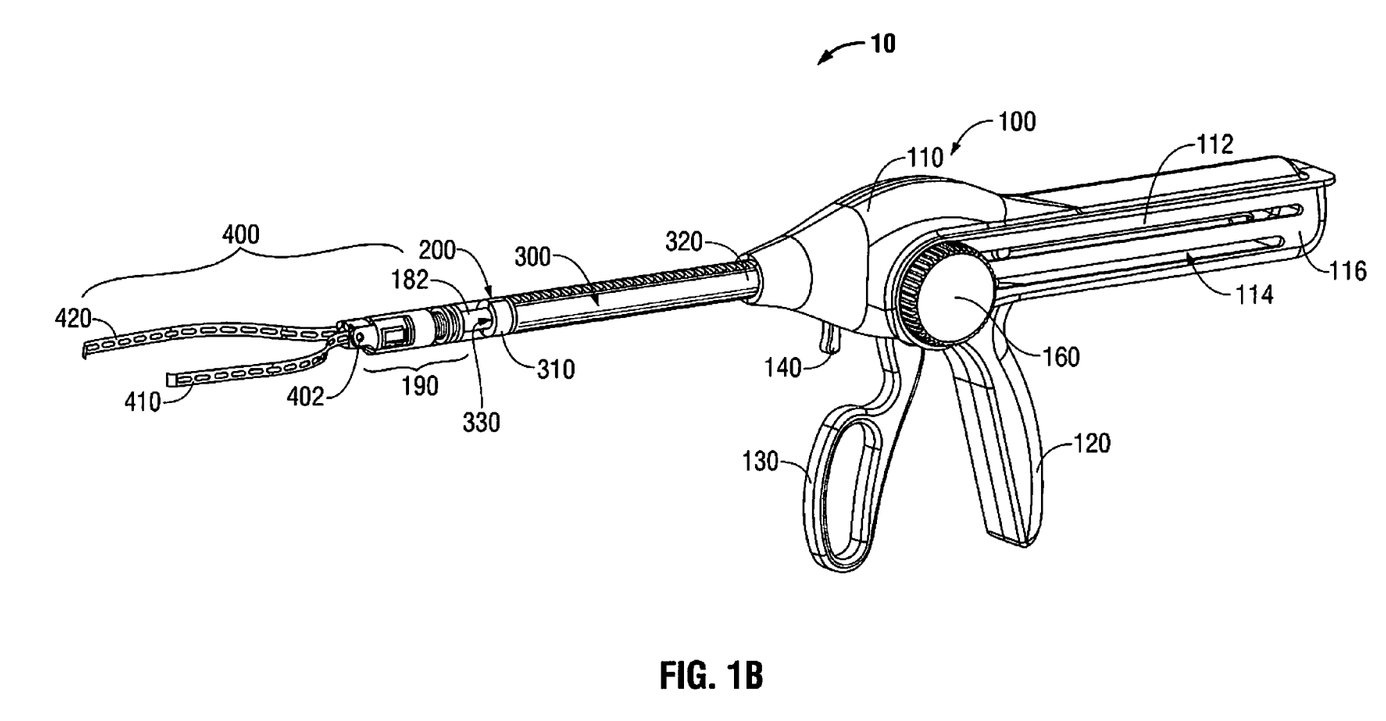
FIG. 1B is a perspective view of the specimen retrieval apparatus of FIG. 1A with the outer sleeve and the retrieval bag removed for clarity and showing the arms expanded.
Figure 2:
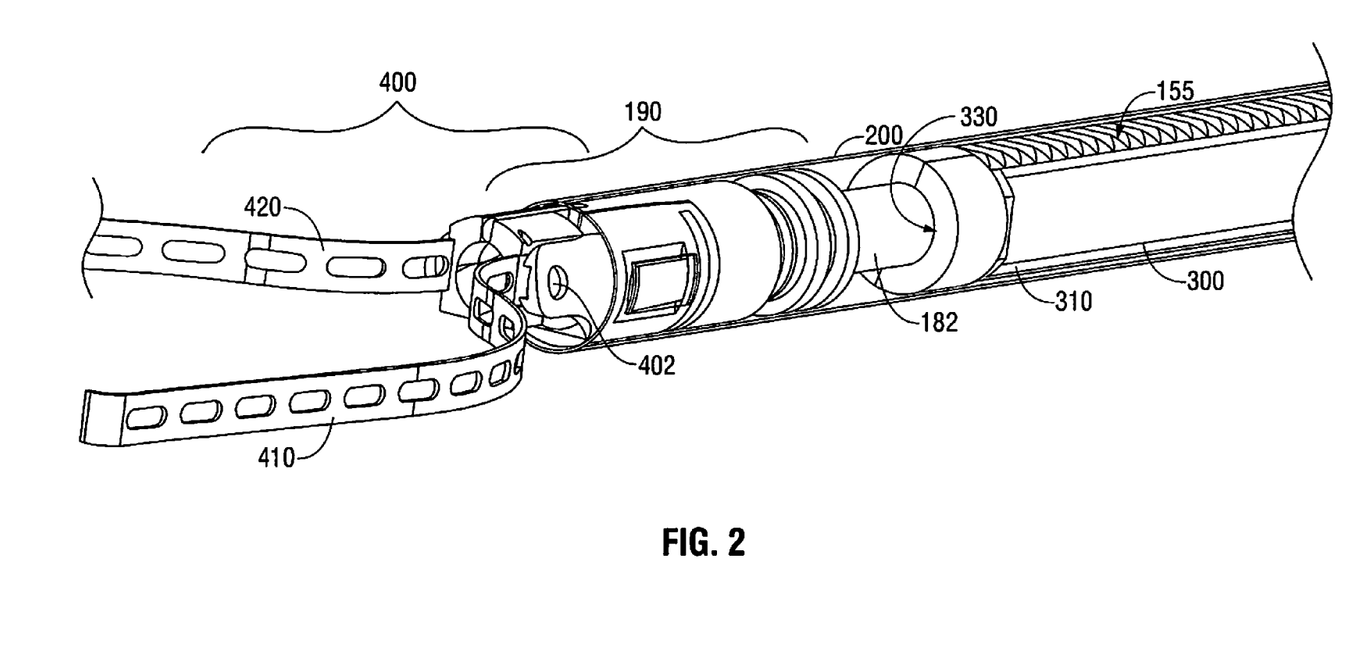
FIG. 2 is an enlarged, perspective view of an end effector of the specimen retrieval apparatus of FIG. 1 (with the retrieval bag not shown for clarity)

Turning now to FIGS. 1A and 1B, a surgical instrument and, more particularly, a specimen retrieval apparatus, is shown designated generally by reference numeral 10. Specimen retrieval apparatus 10 generally includes a handle assembly 100, a sleeve 200, an elongated tubular member 300 disposed within sleeve 200, and an end effector assembly 400 disposed at distal end 310 of elongated tubular member 300. More particularly, sleeve 200 extends distally from handle assembly 100, includes a lumen extending therethrough, and defines a longitudinal axis "X." Elongated tubular member 300 extends through the lumen of sleeve 200 and is positioned about longitudinal axis "X." Proximal end 320 of elongated tubular member 300 extends into handle assembly 100, operatively engaging the internal working components of handle assembly 100. Elongated tubular member 300 includes a lumen 330 (FIG. 3) extending therethrough.

End effector assembly 400 is pivotably engaged to distal end 310 of elongated tubular member 300 via pivot pin 402 such that end effector assembly 400 may be articulated, or pivoted with respect to longitudinal axis "X" and relative to elongated tubular member 300 and sleeve 200. As will be described in greater detail below, end effector assembly 400 is longitudinally translatable between a retracted position, wherein end effector assembly 400 is disposed within sleeve 200 (see FIG. 1A), and an extended position, as shown in FIG. 1B, wherein end effector assembly 400 extends distally from sleeve 200. End effector assembly 400 includes a pair of support arms 410, 420 configured to support/retain a specimen retrieval bag thereon, such as bag 500, 600 or 600' of FIGS. 9A-9B.

With continued reference to FIGS. 1A and 1B, handle assembly 100 generally includes a housing 110, a fixed handle 120, a moveable handle or trigger 130, a release trigger 140 and a rotatable actuator 160. Moveable handle 130 is selectively depressible from a spaced-apart position relative to fixed handle 120, to a more approximated position relative to fixed handle 120 for moving end effector assembly 400 from the retracted position to the extended position. In the extended position, as shown in FIG. 1B, arms 410, 420 of end effector assembly 400 extend distally from sleeve 200 and define a spaced-apart, curvate configuration for retaining specimen retrieval bag 500 in an open position (see FIG. 12A) thereon, although other configurations, e.g., end effector assembly 400 may include linear arms 410, 420 (see FIGS. 6A and 6C), are also contemplated. As will be described in greater detail below, moveable handle 130 is configured for translating end effector assembly 400 from the retracted position to the extended position or to any one of a plurality of incremental positions therebetween. Release trigger 140, when depressed, returns moveable handle 130 to the spaced-apart position permitting end effector assembly 400 to be returned to the retracted position. Preferably, handle 130 is biased to its spaced position of FIG. 1A.

Figure 7:
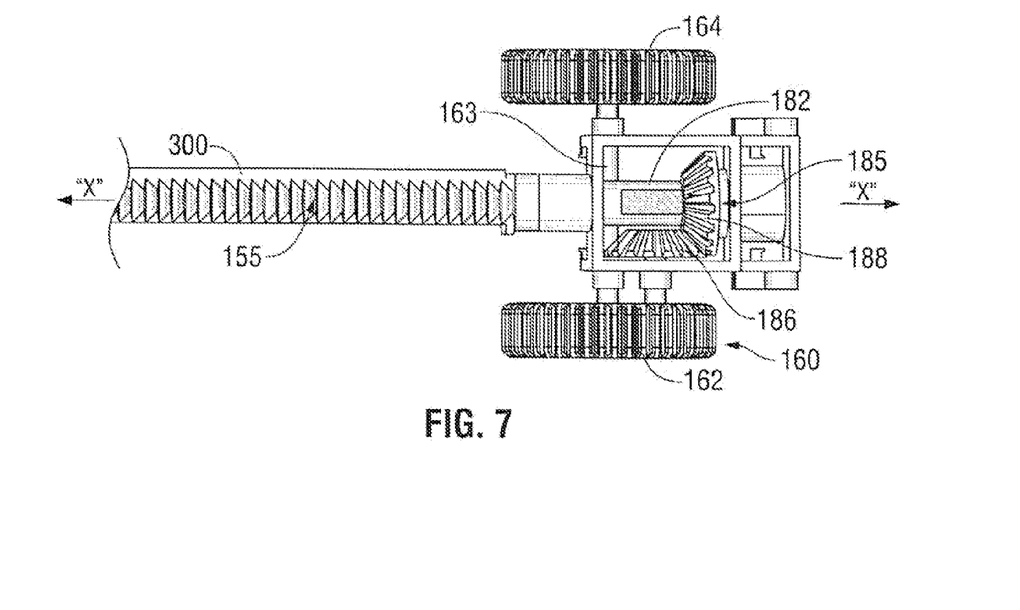
FIG. 7 is a top, cross-sectional view of a proximal portion of the articulation mechanism.
Figure 8:
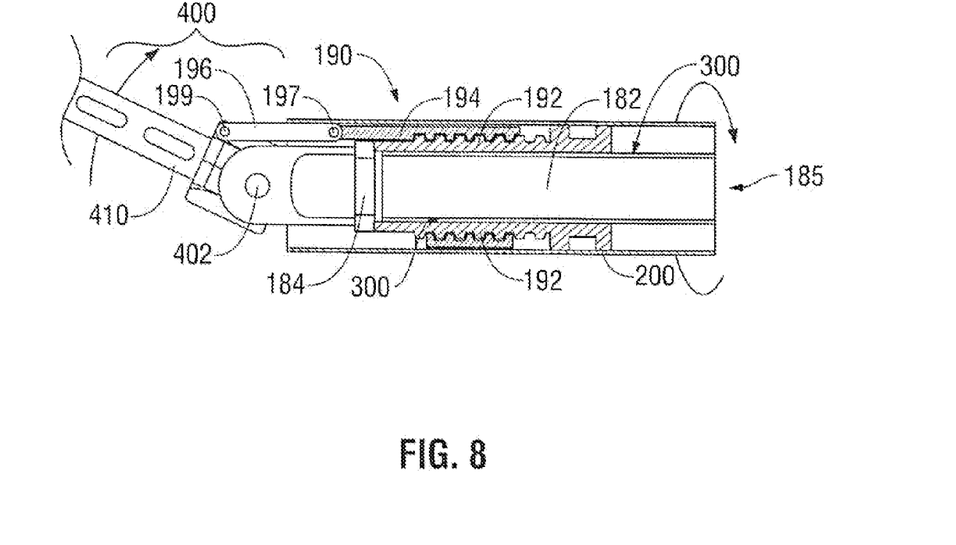
FIG. 8 is a side cross-sectional view of a distal portion of the articulation mechanism.

Housing 110 of handle assembly 100 houses the internal working components of specimen retrieval apparatus 10 and includes rotatable actuator 160 disposed thereon. Rotatable actuator 160 may be disposed on one side of housing 110 or, as shown in FIGS. 7 and 8, may include first and second rotatable portions 162, 164, respectively, disposed on either side of housing 110 and interconnected by an axle 163. As will be described in greater detail below, rotatable actuator 160 is selectively rotatable to articulate end effector assembly 400 with respect to longitudinal axis "X" and is selectively translatable with respect to housing 110 from a distal position to a proximal position to retract end effector assembly 400.

Housing 110 further includes an elongated proximal portion 112 defining a slot 114 extending therealong. Slot 114 of elongated proximal portion 112 of housing 110 permits translation of rotatable actuator 160 from the distal position shown in FIGS. 1B and 12A along slot 114 to a proximal position at proximal end 116 of elongated proximal portion 112 of housing 110 (see FIGS. 1A and 12B). Translation of rotatable actuator 160 from the distal position to the proximal position returns end effector assembly 400 to the retracted position. Translation from the proximal to the distal position occurs initially, with deployment of the retrieval bag (and end effector assembly). More particularly, upon translation of rotatable actuator 160 from the distal position to the proximal position, end effector assembly 400 is translated proximally back into sleeve 200 such that arms 410, 420 are similarly retracted back into sleeve 200 and are moved to an approximated position with respect to one another due to the internal dimensions of sleeve 200. Arms 410, 420 can be biased to an expanded or spaced position such that when free of the confines of sleeve 200, automatically move to the expanded position of FIG. 1B.

Referring now to FIGS. 2-5, the drive assembly 150 of specimen retrieval apparatus 10, which effects translation of end effector assembly 400 from the retracted position to the extended position, will be described. Drive assembly 150 is substantially disposed within housing 110 of handle assembly 100 and includes a drive shaft 152. As mentioned above, elongated tubular member 300 of surgical instrument 10 is engaged to end effector assembly 400 at a distal end 310 thereof and extends proximally through sleeve 200 into housing 110 of handle assembly 100. Drive shaft 152 engages elongated tubular member 300 within housing 110 and includes a lumen 153 extending therethrough in communication with lumen 330 of elongated tubular member 300. As will be described below, the lumen of drive shaft 152 and lumen 330 of elongated tubular member 300 cooperate to permit passage of articulation rod 182 therethrough (FIG. 6A).

Figure 3:
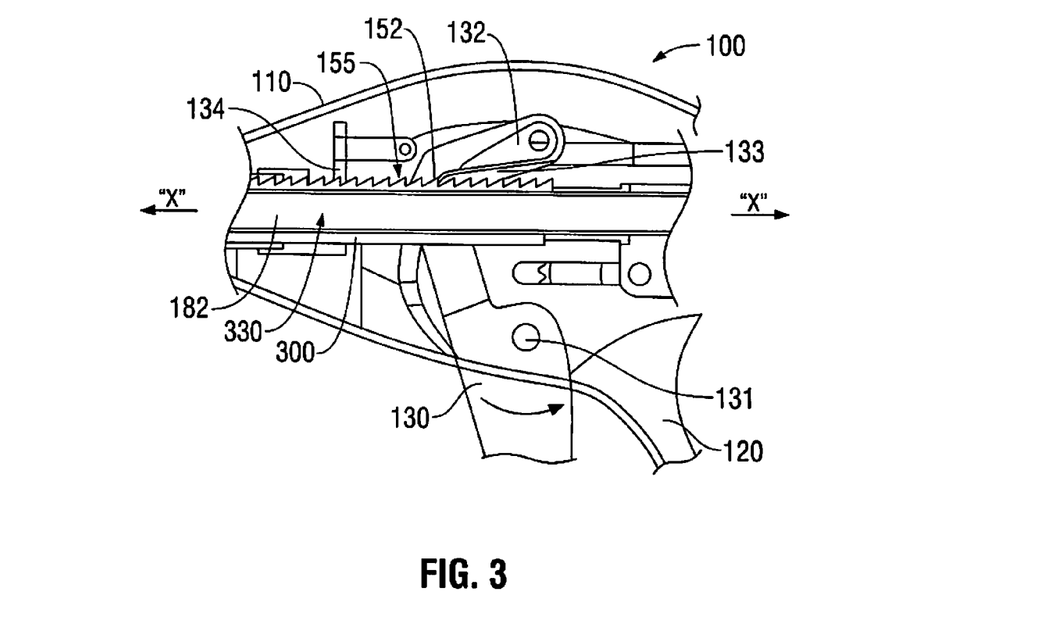
FIG. 3 is side, cross-sectional view of the handle assembly of the specimen retrieval apparatus of FIG. 1.

Drive shaft 152 includes a plurality of teeth or notches 155 disposed thereon and extending longitudinally therealong. Each of notches 155 defines a distal surface and a proximal surface. The distal surfaces of notches 155 define a sloped configuration, while the proximal surfaces of notches 155 are substantially perpendicular with respect to longitudinal axis "X," as best shown in FIG. 3. As will be described below, these notches 155 are selectively engageable to permit incremental distal advancement of drive shaft 152 which, in turn, effects incremental distal translation of elongated tubular member 300 and, thus, end effector assembly 400 from the retracted position to the extended position. In other words, notches 155 of drive shaft 152 and lever 134 of moveable handle 130 cooperate to form a ratchet-like mechanism for selectively advancing end effector assembly 400.

Figure 4:
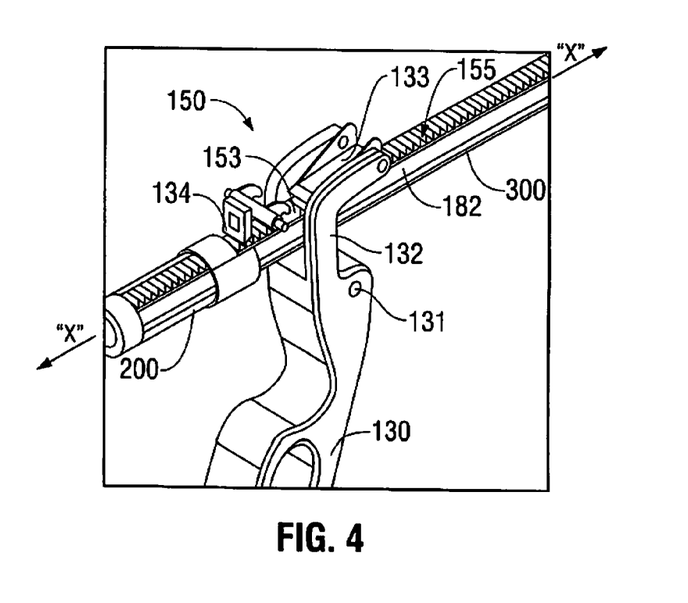
FIG. 4 is a perspective view of the trigger shown coupled to a drive shaft of the specimen retrieval apparatus.
Figure 5:
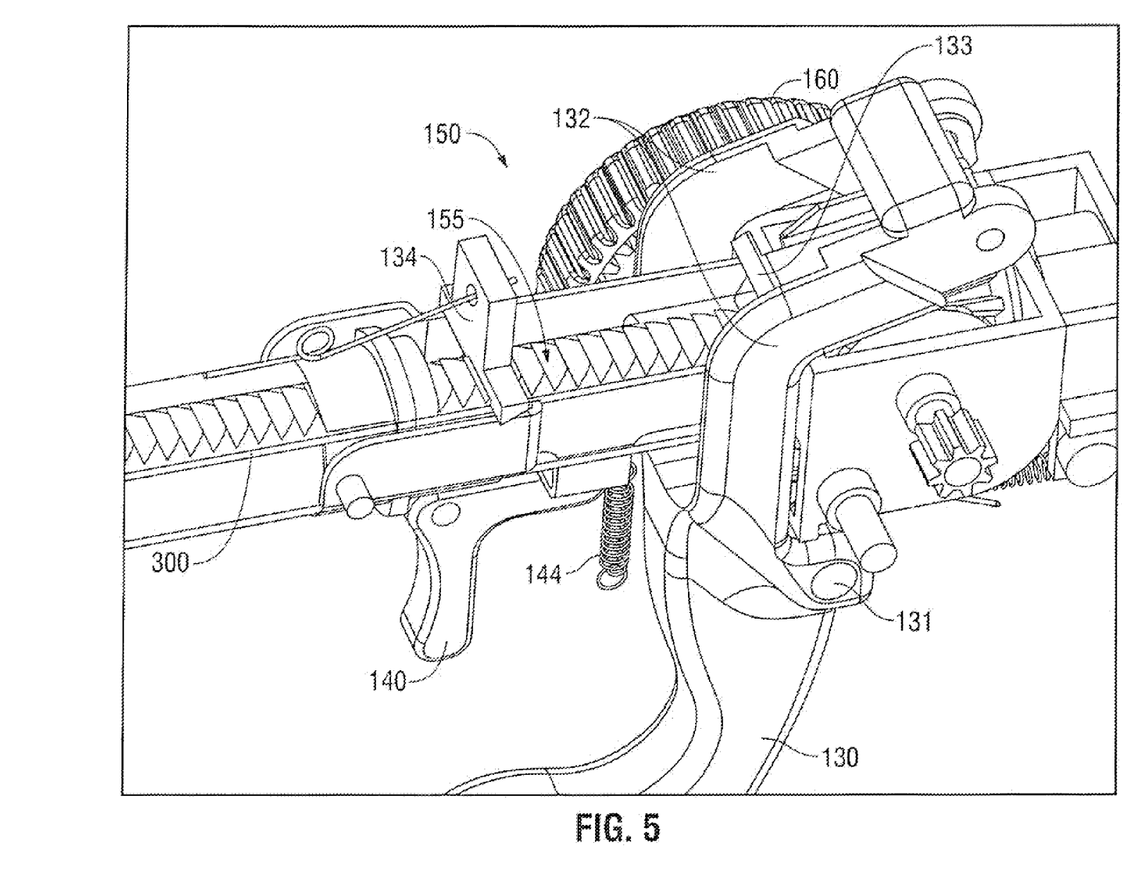
FIG. 5 is a perspective view of a portion of the handle assembly (with parts removed for clarity)
Figures 6A, 6B, 6C:
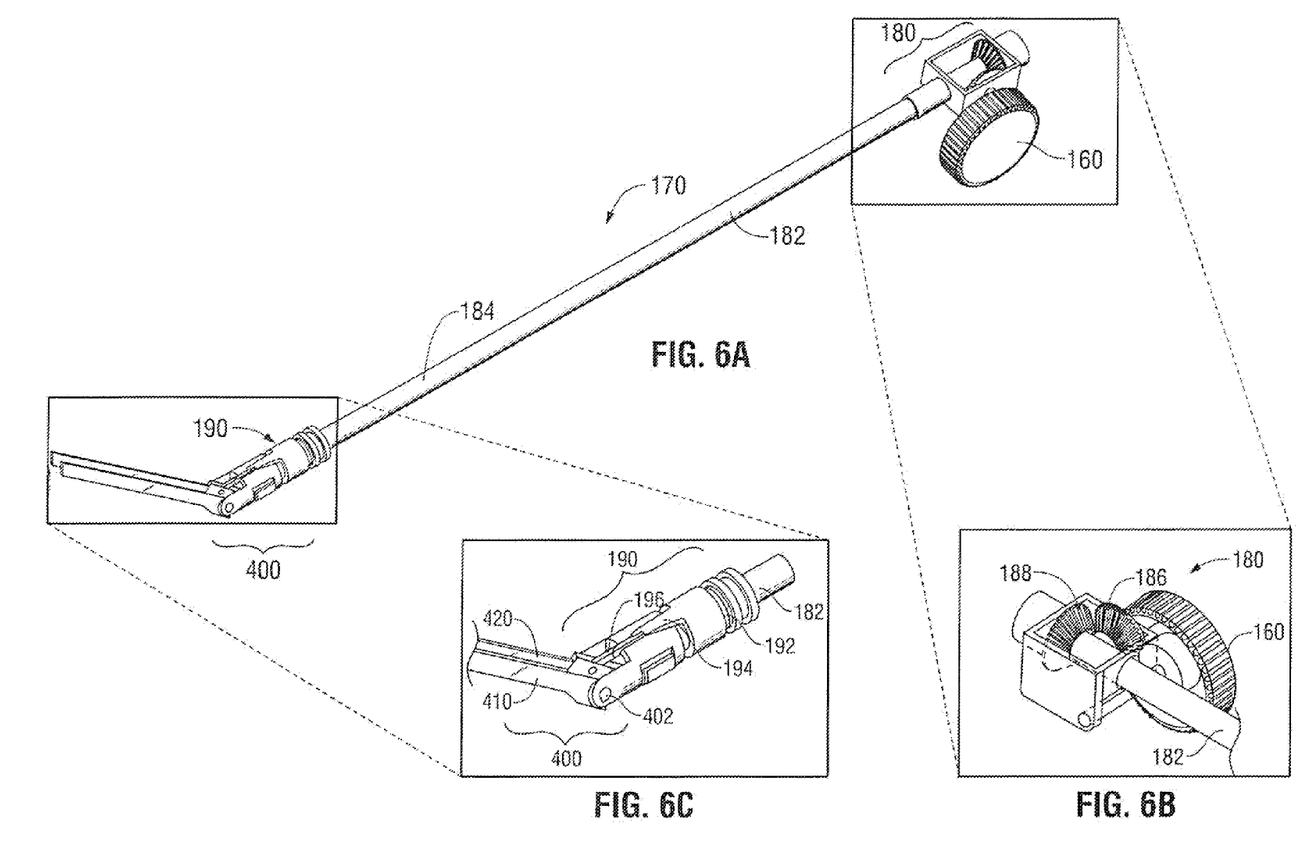
FIG. 6A is a perspective view of the drive shaft of the specimen retrieval apparatus including an articulation mechanism coupled thereto for articulating the end effector assembly with respect to the drive shaft.
FIG. 6B is an enlarged perspective view of the area of detail of FIG. 6A.
FIG. 6C is an enlarged perspective view of the area of detail of FIG. 6A.

As best shown in FIGS. 3-5, moveable handle 130, which extends downwardly from housing 110 of handle assembly 100, includes a U-shaped flange 132 that is pivotably coupled to housing 110 such that moveable handle 130 may be pivoted, or moved between the spaced-apart position and the approximated position with respect to fixed handle 120. U-shaped flange 132 of moveable handle 130 further includes a lever 134 configured for selectively engaging notches 155 of drive shaft 152. More particularly, due to the saw-toothed configuration of notches 155, lever 134 is translatable proximally along drive shaft 152, i.e., lever 134 ramps up over the sloped distal surfaces of notches 155. However, lever 134 is inhibited from translating distally along drive shaft 152 due to the substantially perpendicular proximal surfaces of notches 155, i.e., lever 134 is inhibited from traversing the proximal surfaces of notches 155. Thus, as can be appreciated, upon depression, or proximal pulling of moveable handle 130, i.e., from the spaced-apart position relative to fixed handle 120 to the approximated position relative to fixed handle 120, lever 134 is moved proximally with respect to drive shaft 152 (ramping over notches 155), incrementally engaging each of notches 155 and, in turn, urging drive shaft 152 distally which, in turn, translates elongated tubular member 300 and end effector assembly 400 distally from sleeve 200 toward the extended position.

Referring again to FIGS. 2-5 and as mentioned above, the plurality of notches 155 disposed along drive shaft 152 permit incremental advancement of drive shaft 152 as lever 134 of moveable handle 130 is engaged with each successive notch 155. Accordingly, moveable handle 130 may be depressed from the spaced-apart position to the approximated position with respect to fixed handle 120 to incrementally translate end effector assembly 400 from the retracted position to the extended position or to any of the incremental positions therebetween. As can be appreciated, the incremental "steps" of advancement of end effector assembly 400 are defined by the configuration and spacing of notches 155. As such, surgical instrument 10 and, more particularly, drive shaft 152, may be configured to achieve a desired increment of advancement of end effector assembly 400, e.g., drive shaft 152 may be configured for finer adjustment (smaller increments), or for greater distal advancement per increment (larger increments).

Release trigger 140, as mentioned above, is configured to return moveable handle 130 to the spaced-apart position. More specifically, release trigger 140, connected to lever 134, when depressed, disengages lever 134 of U-shaped flange 132 from notches 155 of drive shaft 152 such that moveable handle 130 may translate distally along drive shaft 152 back to the spaced-apart position. When release trigger 140 is released, lever 134 is re-engaged to drive shaft 152.

Turning now to FIGS. 6A-8, the articulation mechanism 170 of specimen retrieval apparatus 10 will be described. As shown in FIGS. 6A-6C, articulation mechanism 170 includes a rotatable actuator assembly 180 disposed at proximal end 183 of articulation rod 182. Articulation rod 182 extends distally through lumens 153 and 330 of drive shaft 152 and tubular member 330, respectively, and engages articulation assembly 190, which is coupled to end effector assembly 400 at a distal end 184 of articulation rod 182. Articulation rod 182 further includes a lumen 185 extending therethrough. Lumen 185 of articulation rod 182, as will be described below, can be configured for passage of additional surgical instrumentation, e.g., a vacuum tube 600 (FIG. 10B), therethrough in certain embodiments.

Rotatable actuator 160 of rotatable actuator assembly 180, as mentioned above, includes first and second rotatable wheels 162, 164, respectively, disposed on either side of housing 110 of handle assembly 100. Actuator axle 163 extends through housing 110 of handle assembly 100 to couple first and second rotatable wheels 162, 164, respectively, to one another. Rotatable actuator 160 is operably coupled to articulation rod 182 of rotatable actuator assembly 180. More specifically, rotatable actuator assembly 180 includes first and second gear members 186, 188, respectively, configured for rotating articulation rod 182 about longitudinal axis "X" upon rotation of rotatable actuator 160. First gear 186 is engaged to rotatable actuator 160, while second gear 188 is engaged to articulation rod 182. First and second gears 186, 188, respectively, are disposed in meshed engagement with one another such that rotation of rotatable actuator 160 effects rotation of articulation rod 182 about longitudinal axis "X."

As mentioned above, and as best shown in FIG. 8, articulation rod 182 extends distally through lumen 153 of drive shaft 152 and through lumen 330 of elongated tubular member 300 to engage articulation assembly 190 at distal end 184 of articulation rod 182. Articulation assembly 190 includes a threaded ferrule, or worm gear 192, fixedly engaged to, and disposed about articulation rod 182. A gear rack 194 disposed in meshed engagement with worm gear 192 extends distally therefrom to engage a pivoting linkage 196. Pivoting linkage 196 is pivotably connected at a first end 197 to gear rack 194 and at a second end 199 to end effector assembly 400, preferably by a rivet or pin, although other attachment methods are also contemplated. The threading of worm gear 192 is pitched such that upon rotation of articulation rod 182 and, thus, worm gear 192, gear rack 194 is translated longitudinally along worm gear 192. Thus, as can be appreciated, when worm gear 192 is rotated about longitudinal axis "X," e.g., due to the rotation of rotatable actuator 160 and, thus, articulation rod 182, gear rack 194 is translated proximally therealong (or distally therealong, depending on the direction of rotation of articulation rod 182). As gear rack 194 is translated proximally, pivoting linkage 196 is likewise translated proximally. The proximal translation of pivoting linkage 196 pulls end effector assembly 400 toward pivoting linkage 196 (upwardly in the orientation of FIG. 8) such that end effector assembly 400 is pivoted about pivot pin 402 to articulate, or angle off of longitudinal axis "X," as shown in FIG. 8.

As can be appreciated, further rotation of articulation rod 182 effects further articulation of end effector assembly 400, as pivoting linkage 196 pulls end effector assembly 400 further proximally. Thus, end effector assembly 400 may be articulated with respect to longitudinal axis "X" between an aligned position, wherein end effector assembly 400 is positioned substantially along longitudinal axis "X," to a substantially perpendicular position, wherein end effector assembly 400 is articulated or angled about 90 degrees with respect to longitudinal axis "X," or at any angle therebetween. In order to return end effector assembly 400 to the aligned position, rotatable actuator 160 is rotated in the opposite direction to effect rotation of articulation rod 182 about longitudinal axis "X" in the opposite direction. As such, worm gear 192 is rotated to translate gear rack 194 distally therealong, urging pivoting linkage 196 distally and, thus, pivoting end effector assembly 400 back toward the aligned position.

With continued reference to FIG. 8, end effector assembly 400 may be configured such that articulation of end effector assembly 400 is inhibited when end effector assembly 400 is in the retracted position. More specifically, when end effector assembly 400 is disposed within sleeve 200, end effector assembly 400 is inhibited from substantially pivoting, or articulating about pivot pin 402 off of longitudinal axis "X" due to the internal dimensions of sleeve 200. However, when end effector assembly 400 is translated to the extended position such that end effector assembly 400 extends distally from sleeve 200 (as best shown in FIG. 8), end effector assembly 400 is free to pivot upon distal translation of pivoting linkage 196 and, thus, may be articulated off of longitudinal axis "X."

Referring now to FIG. 1, in conjunction with FIGS. 6A-6C, as mentioned above, rotatable actuator assembly 180 is selectively translatable along slot 114 of elongated proximal portion 112 of housing 110 from the proximal position shown in FIG. 1A (at proximal end 16), to the distal position at elongated proximal portion 112 of housing 110 shown in FIG. 1B. Assembly 180 and wheel 160 slide forward together as the ratchet moves the inner assembly forward, deploying the bag. Rotatable actuator assembly 180 is in the distal position as end effector assembly is deployed from sleeve 200. Translation from the distal position to the proximal position pulls end effector assembly 400 proximally, thus returning end effector assembly 400 to the retracted position within sleeve 200. That is, as rotatable actuator assembly 180 is translated proximally, articulation rod 182 is translated proximally, which, in turn, translates drive shaft 152, elongated tubular member 300, and end effector assembly 400 proximally to the retracted position within sleeve 200. The use and operation of specimen retrieval apparatus 10 will be described in greater detail below.

Figure 9A:
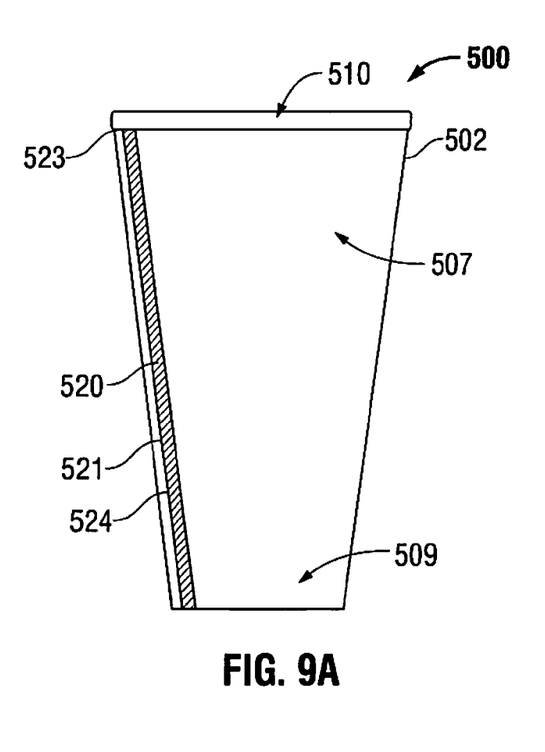
FIG. 9A is a side cross-sectional view of one embodiment of a specimen retrieval bag configured for use with the specimen retrieval apparatus of FIG. 1.
Figure 9B:
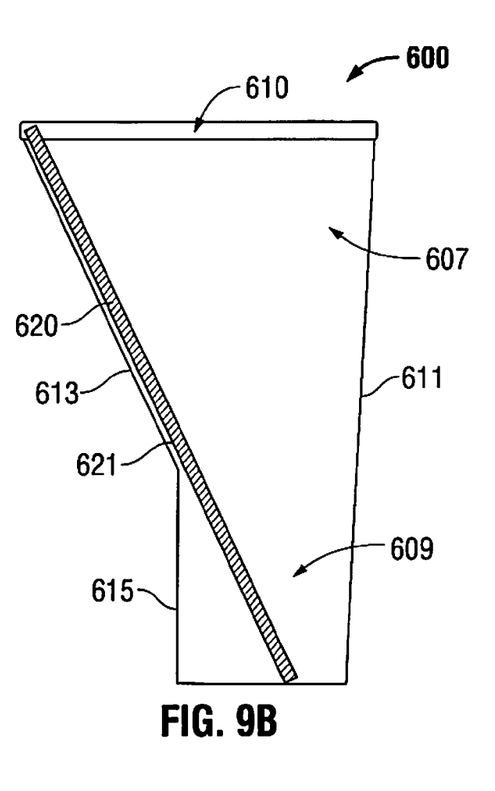
FIG. 9B is a side cross-sectional view of another embodiment of a specimen retrieval bag configured for use with the specimen retrieval apparatus of FIG. 1.
Figure 9C:
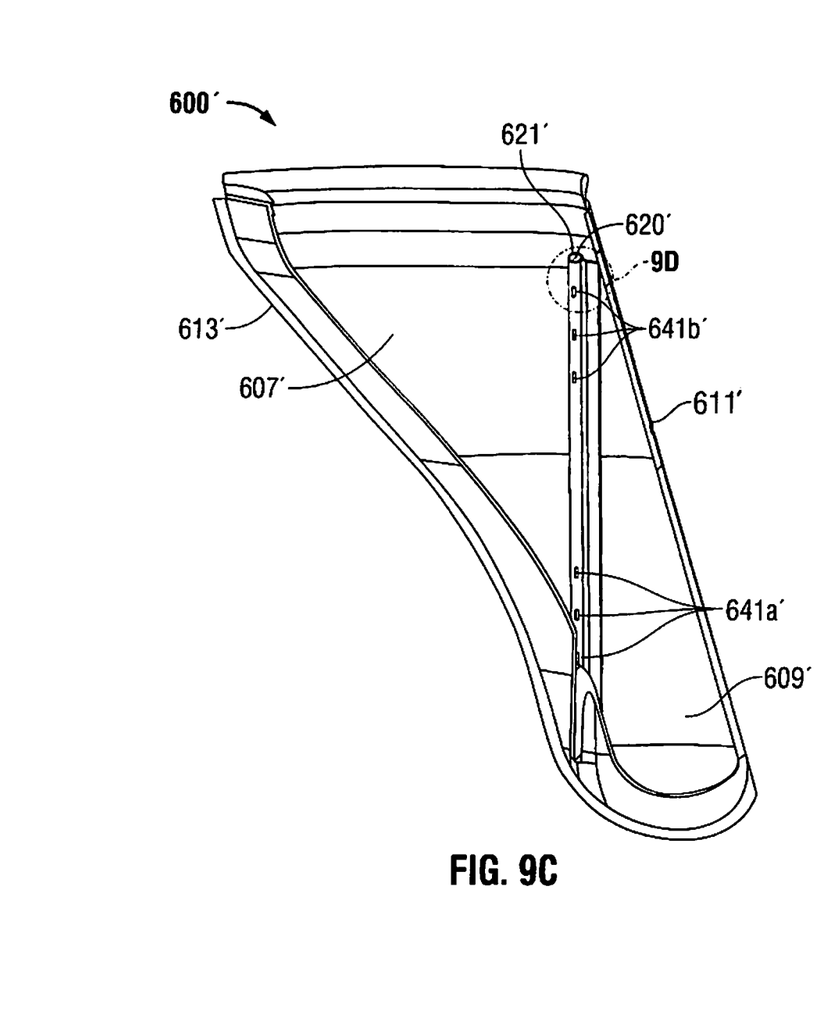
FIG. 9C is a side view of another embodiment of a specimen retrieval bag configured for use with the specimen retrieval apparatus of FIG. 1.

Turning now to FIGS. 9A, 9B and 9C, embodiments of the specimen retrieval bag are shown. The specimen retrieval bag may be formed from any suitable bio-compatible material (or materials) configured to retain a tissue specimen therein. Specimen retrieval bag 500 may include a high-friction mesh material disposed on an inner surface thereof to facilitate retention of a specimen of tissue therein.

FIG. 9A shows one embodiment of a specimen retrieval bag. Specimen retrieval bag 500 is folded over to form a channel, or loop 510 at open end 502 thereof. Arms 410, 420 of end effector assembly 400 (FIG. 1B) are positionable at least partially through loop 510 of specimen retrieval bag 500 to retain specimen retrieval bag 500 thereon. Preferably, retrieval bag 500 is removably retained by arms 410, 420.

Specimen retrieval bag 500 further includes a channel 521 along the inner wall. The channel 521 (and channel 621 and 621' discussed below) can be formed as integral with the bag material or alternatively can be in the form of a separate tube or separate material attached to the bag 500, e.g. attached to an inner surface. The separate material can be different or the same as the bag material. The channel 521 includes at least one opening or slot 524 to allow the passage of air into the channel 521. Preferably, a plurality of spaced apart slots or openings are provided along the length to enable communication between the air and/or fluid in the bag 500 and the interior of the channel 521 such as in channel 621' discussed below. The channel 521 (and channels 621 and 621' discussed below) in some embodiments can also terminate at its distal end spaced from the bottom of the bag 500 to communicate at a distal opening of the channel with the interior of the bag to provide another path for the escape of air and/or fluid. Proximal end 523 of the channel 521 is open to communicate with the exterior of the bag, but can alternately terminate more distally to communicate with a proximal interior of the bag.

Positioned within the channel 521 is a support member (or support members) 520 configured for preventing collapse of the channel 521. It can also in some embodiments be utilized to bias the specimen retrieval bag 500 in an open position upon deployment from specimen retrieval apparatus 10, i.e., upon translation of end effector assembly 400 from the retracted position to the extended position. Support member 520 may be formed from, for example, an open cell material, such as open cell foam, or other suitable material. The support member 520 is elongated and can extend the full length or alternatively the partial length of the channel. The support member 520 (and channel) also illustratively extend at an angle to a longitudinal axis of the bag 500 as shown. The open cell foam enables the passage of air and/or fluid. The open cell foam is preferably of a transverse cross-section less than the transverse cross-section of the channel 521. In this manner, air and/or fluid entering the channel 521 from the bag 500 can flow around the foam material through the channel 521. Note that due to the open cell foam, the air or fluid can also flow through the open cell foam itself. This way, if the channel 521 collapses or is compressed during specimen retrieval, air and fluid can still escape from the bottom portion of the bag through the open cell foam. The escape of air and fluid is caused as the pressure is applied to the bag 500 during withdrawal through an access port or body opening. As the bag 500 is compressed, the air and/or fluid is forced proximally through the channel 521, exiting the open proximal end 523 and/or through side slots. Thus, this decrease in pressure prevents balling of the specimen at the bottom of the bag 500 and facilitates removal, and the specimen can take on an elongated sausage-like shape to conform to the elongated incision to facilitate removal.

Specimen retrieval bags 500, 600 and 600', respectively, may be formed in various configurations and/or may include support members 520, 620 and 620', respectively, of varying configuration, depending on the intended use of the specimen retrieval bag 500, 600 and 600'.

In the embodiment of FIG. 9A bag 500 has a reduced transverse dimension at the distal portion. That is, the bag 500 narrows distally so that its transverse dimension at the proximal region 507 adjacent the mouth is greater than a transverse dimension at the distal region 509. As shown, this narrowing can be in the form of a progressive taper.

In the embodiment of FIG. 9B, the bag 600 has proximal region 607 and a distal region 609. Distal region 609 has a smaller transverse dimension than proximal region 607. In the illustrated embodiment, bag 600 has a first side 611 and an angled side 613 in the proximal region 507 opposite the first side 611. This side 613 tapers inwardly such that the transverse dimension of proximal region 607 progressively decreases toward the distal region 609. Wall 615 opposite the wall 611 in the distal region 609 extends substantially parallel to the wall 611. Thus, as can be appreciated, the transverse dimension remains substantially the same in the distal region 609, but is smaller than the transverse dimension in the proximal region 607. Other shaped bags are also contemplated. Bag 600 includes an interior channel 621 with one or more slots as in channel 521 of FIG. 9A and/or as in channel 621' of FIG. 9C, with a support member 620 of an open cell material, such as open cell foam, as in FIG. 9A. The channel 621 and support member 620 are shown at an acute angle to a longitudinal axis of the bag 600 and extending through the proximal and distal regions 607, 609. As with support member 520, the support member 620 can extend the entire length or alternatively a partial length of the channel. The proximal end of the channel can terminate distal of the mouth of the bag to communicate with a proximal interior of the bag. The channel 621 and support member 620 function in the same manner as channel 521 and support member 520 and therefore for brevity are not further discussed herein.

Figure 9D:
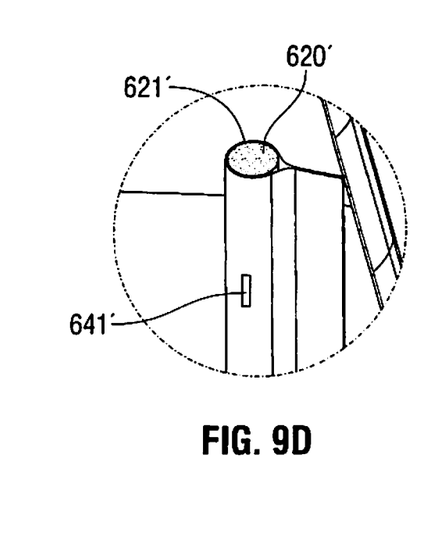
FIG. 9D is an enlarged view of the area of detail of FIG. 9C.

In the embodiment of FIGS. 9C and 9D, retrieval bag 600' has a curved wall 613' opposite wall 611' tapering toward the distal region 609' so the distal region 609' has a smaller transverse dimension than proximal region 607'. Interior channel 621' attached to bag 600' has a support member 620' of open cell material, such as open cell foam. Other materials are also contemplated. The open cell material 620' (and 620) is preferably of a transverse cross-section less than the transverse cross-section of the channel 621' (or 621). Slots 641a' in the lower region of channel 621' enable passage of air from the bottom of bag 600' into the channel 621' to exit slots 641b' in the upper region of channel 621' into the interior proximal region of bag 620'. Such arrangement of slots or alternatively other arrangements and or alternative numbers of slots can be provided in the various retrieval bags disclosed herein.

Specimen retrieval bags 500, 600 further include a cinch strings of cord 550 (FIG. 11) disposed through loops 510, 610, respectively, for cinching closed specimen retrieval bags 500, 600 to enclose the tissue specimen therein. In either embodiment, specimen retrieval bag 500, 600 is positionable on arms 410, 420 (FIG. 1B) of end effector assembly 400 and is configured for transitioning between a retracted position within sleeve 200, when end effector assembly 400 is in the retracted position, and an open, extended (deployed) position, when end effector assembly 400 is moved to the extended position and arms 410, 420 move to a spaced position.

Figure 10A:
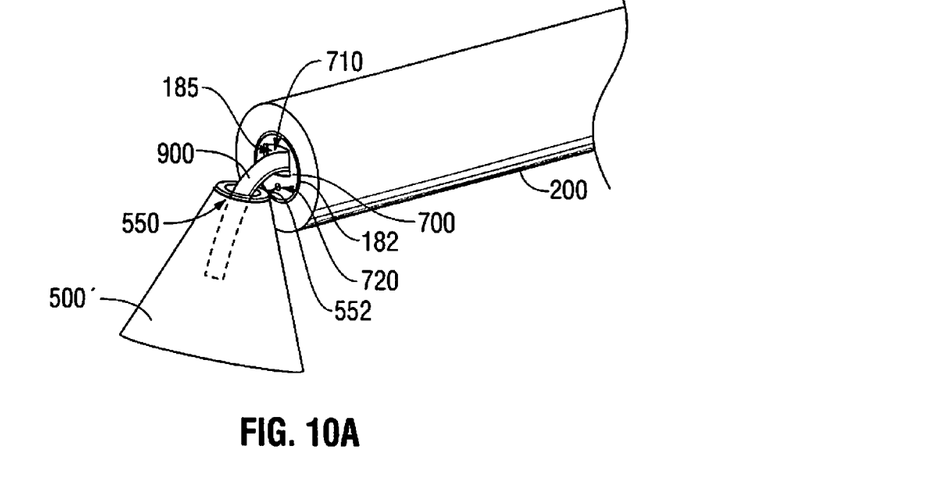
FIG. 10A is a perspective view of a distal end of an alternate embodiment of the specimen retrieval apparatus having a vacuum tube extending through an end cap and into the specimen retrieval bag.
Figure 10B:
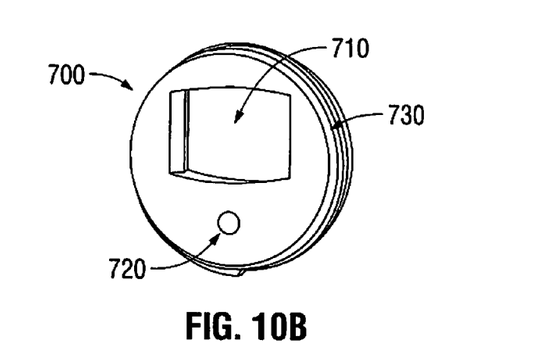
FIG. 10B is a perspective view of the end cap of the specimen retrieval apparatus of FIG. 10A.

With reference now to FIGS. 10A and 10B, an alternate embodiment of the specimen retrieval apparatus is shown having an end cap 700 for positioning within lumen 330 of elongated tubular member 300 at distal end 310 thereof. As mentioned above, articulation rod 182 is disposed within lumen 330 of elongated tubular member 300 and includes a lumen 185 extending therethrough. Accordingly, surgical instrumentation, e.g., vacuum tube 900, may be inserted from the proximal end of specimen retrieval apparatus 10 and through lumen 185 of articulation rod 182 to extend distally from lumen 185 of articulation rod 182 and lumen 330 of elongated tubular member 300 adjacent end effector assembly 400 such that vacuum tube 900 may be positioned adjacent specimen retrieval bag 500 (or bag 600). More particularly, end cap 700 includes a window 710 defined therein to permit vacuum tube 900 (or other surgical instrumentation) to extend distally from elongated tubular member 300, while inhibiting other materials and/or debris from entering lumen 330 of elongated tubular member 300. An aperture 720 defined through end cap 700 is configured for passing of cinch string 550 therethrough. End cap 700 may also include threading 730 disposed on an outer circumferential surface thereof for engaging elongated tubular member 300, or may be configured to engage elongated tubular member 300 in any other suitable fashion, e.g., snap fit, friction fit, etc.

As best shown in FIG. 10A, vacuum tube 900 includes a curved distal tip such that vacuum tube 900 extends at least partially into specimen retrieval bag 500' when extending through window 710 of end cap 700. Such configuration permits vacuum tube 900 to extend into specimen retrieval bag 500' for suctioning or vacuuming out the excess air, fluid and/or debris from within specimen retrieval bag 500' once specimen retrieval bag 500' has been cinched closed, reducing the overall size of specimen retrieval bag 500' and, thus, facilitating removal of the specimen retrieval bag 500' from the body. Vacuum tube 900 may be biased toward this curved configuration such that, as vacuum tube 900 is extended from lumen 330 of elongated tubular member 300, vacuum tube 900 returns to the curved configuration shown in FIG. 10A. Vacuum tube 900 may be formed at least partially from a shape-memory material, e.g., nitinol, to achieve the curved distal tip shown in FIG. 10A. This embodiment with the vacuum tube 900 can be utilized as an alternative to the channels 521,621 of FIGS. 9A and 9B, or used as a supplement to the channels.

Figure 11:
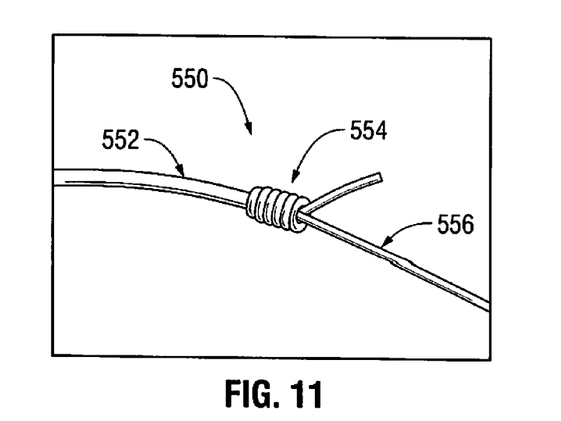
FIG. 11 is a perspective view of a cinch cord for use with the specimen retrieval apparatus of FIG. 1.

Turning now to FIG. 11, cinch cord 550 is shown. Cinch cord 550 includes a looped portion 552, a knot portion 554, and a proximal portion 556. Looped portion 552 of cinch cord 550 is configured to be positioned through loop 510 of specimen retrieval bag 500 see (e.g FIG. 9A) which can be in the form of a channel in the bag formed for example by a fold. Knot portion 554 is configured as a one-way knot and is configured to reduce the diameter of looped portion 552 and, thus, to cinch close the specimen retrieval bag, e.g. bag 500, upon proximal pulling of proximal portion 556. In the embodiment of FIG. 10A, proximal portion 556 extends through aperture 720 of end cap 700 and is fixedly engaged to elongated tubular member 300 (or another structure disposed therein) such that, upon proximal translation of elongated tubular member 300, e.g., due to the translation of rotatable actuator 160 along slot 114 of housing 110 from the distal position to the proximal position to retract end effector assembly 400, proximal portion 556 is pulled proximally thereby reducing looped portion 552 to cinch closed specimen retrieval bag 500. The one-way configuration of knot portion 554 inhibits looped portion 552 from opening and, thus, inhibits the specimen retrieval bag (e.g bag 500) from opening, once it has been cinched closed. It is envisioned that the specimen retrieval bag and cinch cord 550 cooperate to effect fluid-tight closure of open end 502 of specimen retrieval bag 500 (or the open ends of other retrieval bags). In the embodiment of FIG. 10A utilizing a vacuum tube 900, the cinch cord 550 closes the retrieval bag 500' about vacuum tube 900 such that vacuum tube 900 may then be used to evacuate the extra area within specimen retrieval bag 500'.

The use and operation of specimen retrieval apparatus 10 will now be described with reference to FIGS. 12A-12C. The apparatus described utilizes bag 500, but bags 600 or 600' could also be utilized and the method described below is fully applicable to instruments with these bags. Initially, specimen retrieval apparatus 10 is disposed in the retracted position such that end effector assembly 400 and specimen retrieval bag 500 (or bag 500' or 600) are substantially disposed within sleeve 200 (as illustrated in FIG. 1A). In this position, specimen retrieval apparatus 10 may be inserted through a relatively small opening in the body, e.g., an access port or cannula, such that end effector assembly 400 is positioned within an internal body cavity adjacent the tissue specimen "S" to be retrieved.

Figure 12A:
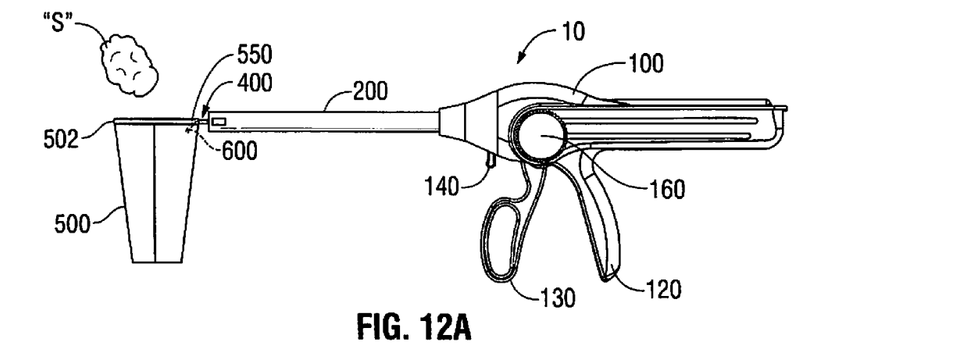
FIG. 12A is a schematic illustration of the specimen retrieval apparatus of FIG. 1 in position to receive a specimen within the specimen retrieval bag.

Once specimen retrieval apparatus 10 is positioned as described above, moveable handle 130 may be pivoted, or pulled proximally to the approximated position with respect to fixed handle 120 to move end effector assembly 400 from the retracted position to the extended position and to deploy specimen retrieval bag 500, as shown in FIG. 12A. More particularly, moveable handle 130 may be depressed to incrementally advance end effector assembly 400 to the desired position. The actuator 160 also advances. Further, once deployed, rotatable actuator 160 may be rotated to articulate end effector assembly 400 off of longitudinal axis "X," to better position specimen retrieval bag 500. Next, as shown in FIG. 12A, the tissue specimen "S" is moved into the specimen retrieval bag 500, through open end 502 thereof, e.g., via use of a surgical grasper (not shown) or any other suitable mechanism.

Figure 12B:
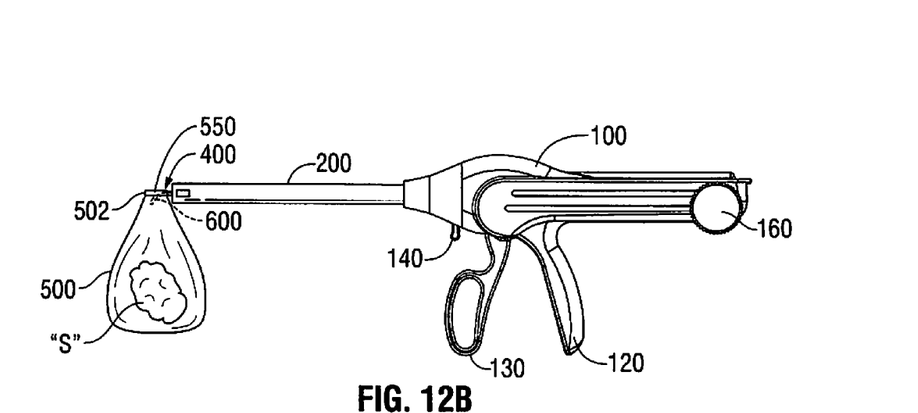
FIG. 12B is a schematic illustration of the specimen retrieval apparatus of FIG. 1 wherein the specimen has been retained within the specimen retrieval bag and the bag shown in a closed condition.

Once the tissue specimen "S" to be retrieved is disposed within specimen retrieval bag 500, as shown in FIG. 12B, specimen retrieval bag 500 may be cinched closed and removed from the internal body cavity. However, in some embodiments, it may first be desired to insert vacuum tube 900 through lumen 185 of articulation rod 182 to extend distally from lumen 330 of elongated tubular member 300 into specimen retrieval bag 500. Once vacuum tube 900 is in position, specimen retrieval bag 500 may be cinched closed about vacuum tube 900 with specimen of tissue "S' therein.

In order to close specimen retrieval bag 500 about specimen of tissue "S," rotatable actuator 160 is translated along proximal portion 112 of housing 110 to return end effector assembly 400 to the retracted position within sleeve 200. As rotatable actuator 160 is translated proximally, elongated tubular member 300 is likewise translated proximally, pulling cinch cord 550 proximally to cinch open end 502 of specimen retrieval bag 500 closed.

Figure 12C:
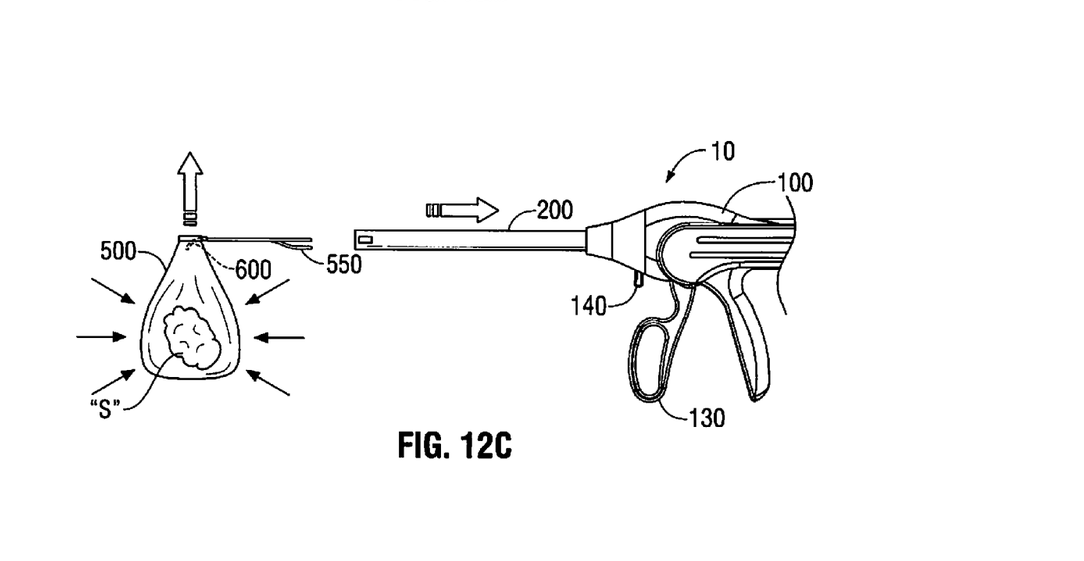
FIG. 12C is a schematic illustration of the specimen retrieval apparatus of FIG. 1 wherein the closed specimen retrieval bag, which includes the specimen disposed therein, has been released from the specimen retrieval apparatus.

As shown in FIG. 12C, once specimen retrieval bag 500 has been cinched closed with tissue specimen "S" disposed therein, specimen retrieval apparatus 10 may be removed from the surgical site. Note that in the embodiment of FIGS. 9A and 9B, the channel 521, 621 enables escape of air to reduce the size of the retrieval bag 500 (or 600) to facilitate removal. In the embodiment of FIG. 10A where vacuum tube 900 is provided, a vacuum or suction source (not shown) may then be engaged to vacuum tube 900 to evacuate specimen retrieval bag 500, minimizing the area therein. The minimized specimen retrieval bag 500, having the tissue specimen "S" disposed therein, may then be removed through the opening, or incision in the body. Note specimen retrieval bag 600 would be open, closed and removed in the same fashion as described above for bag 500.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:
1. A specimen retrieval apparatus, comprising:
 a housing having an elongated tubular member extending distally therefrom, the elongated tubular member defining a longitudinal axis;
 an end effector assembly coupled to a distal end of the elongated tubular member;

a drive assembly operatively engaged to the elongated tubular member and configured for selectively translating the end effector assembly between a retracted position and an extended position;

a trigger pivotably coupled to the drive assembly, the trigger being selectively depressible to incrementally move the end effector assembly from the retracted position to the extended position;

a specimen retrieval bag releasably retained on the end effector assembly;

an articulation mechanism operatively coupled to the end effector assembly, the articulation mechanism configured for selectively incrementally articulating the end effector assembly with respect to the longitudinal axis of the elongated tubular member between an aligned position, wherein the end effector assembly is generally aligned with the longitudinal axis, and an angled position, wherein the end effector assembly is disposed at an oblique angle relative to the longitudinal axis; and a rotatable actuator operably disposed on the housing, coupled to the drive assembly, and coupled to the articulation mechanism, the rotatable actuator being configured for:

incremental translation distally along a translation axis relative to the housing in response to depression of the trigger for moving the end effector assembly from the retracted position towards the extended position;

manual translation proximally along the translation axis relative to the housing to move the end effector assembly from the extended position towards the retracted position; and selective rotation about a rotation axis relative to the housing for articulating the end effector assembly with respect to the longitudinal axis, wherein the rotation axis is translated relative to the housing upon translation of the rotatable actuator along the translation axis relative to the housing.

2. The specimen retrieval apparatus according to claim 1, wherein the articulation mechanism includes a gear rack at a distal portion of the elongated tubular member.

3. The specimen retrieval apparatus according to claim 2, wherein the gear rack is pivotably coupled to the end effector assembly, the gear rack being in meshed engagement with a worm gear such that, upon rotation of the worm gear about the longitudinal axis, the gear rack is translated proximally along the worm gear to articulate the end effector assembly with respect to the longitudinal axis.

4. The specimen retrieval apparatus according to claim 1, wherein the end effector assembly is prevented from being articulated when the end effector assembly is in the retracted position.

5. The specimen retrieval apparatus according to claim 1, wherein the end effector assembly includes a pair of arms configured to retain the specimen retrieval bag thereon, the pair of arms moveable between an approximated position, when the end effector assembly is disposed in the retracted position, and a spaced-apart position, when the end effector assembly is moved to the extended position.

6. The specimen retrieval apparatus according to claim 1, wherein the drive assembly includes a ratchet mechanism for incrementally translating the end effector assembly from the retracted position to the extended position.

7. The specimen retrieval apparatus according to claim 1, wherein the elongated tubular member defines a lumen extending therethrough, the lumen configured to permit passage of surgical instrumentation therethrough.

8. The specimen retrieval apparatus according to claim 7, wherein the lumen of the elongated tubular member is configured to permit passage of a vacuum tube therethrough.

* * * * *